Figure 1A:
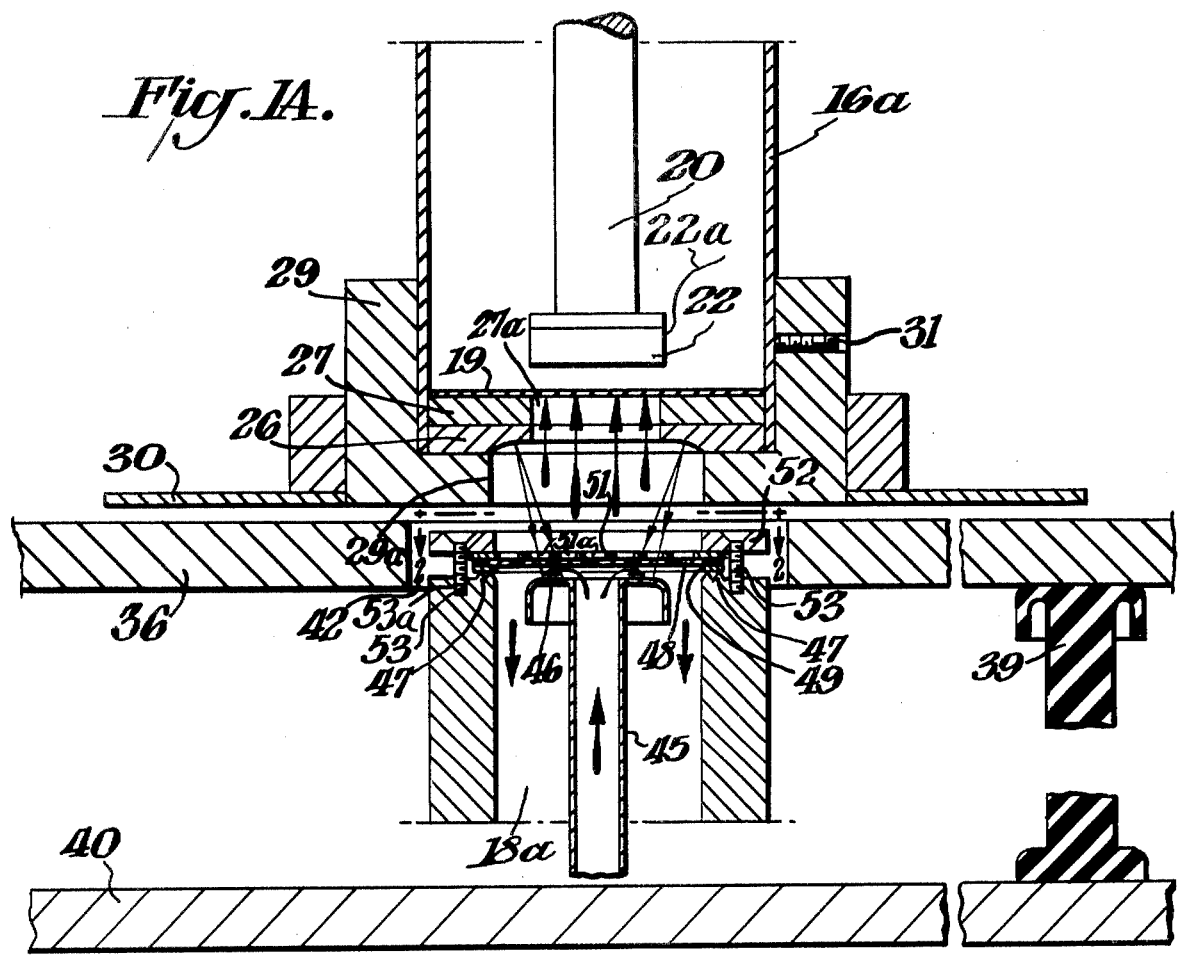

United States Patent [19]

Averitt et al.

[11] 4,152,591

[45] May 1, 1979

[54] ON-STREAM CHEMICAL ELEMENT MONITOR

[75] Inventors: Orman R. Averitt, Newark; Robert R. Dorsch, Wilmington, both of Del.

[73] Assignee: E. I. Du Pont de Nemours and Company, Wilmington, Del.

[21] Appl. No.: 796,749

[22] Filed: May 13, 1977

[51] Int. Cl.² .............................................. G01N 23/20
[52] U.S. Cl. ..................................... 250/273; 250/272
[58] Field of Search ................................ 250/272, 273

[56] References Cited

U.S. PATENT DOCUMENTS

| | | | |
|---|---|---|---|
| 3,742,729 | 7/1973 | Zulliger | 250/272 |
| 4,016,419 | 4/1977 | Kotani et al. | 250/273 |
| 4,063,089 | 12/1977 | Gamba | 250/272 |

*Primary Examiner*—Alfred E. Smith
*Assistant Examiner*—T. N. Grigsby

[57] ABSTRACT

Apparatus and method for on-stream chemical element monitoring wherein a multiplicity of sample streams are flowed continuously through individual analytical cells and fluorescence analyses are performed on the sample streams in sequence, together with a method of controlling the time duration of each analysis as a function of the concomitant radiation exposure of a preselected perforate reference material interposed in the sample-radiation source path.

5 Claims, 5 Drawing Figures

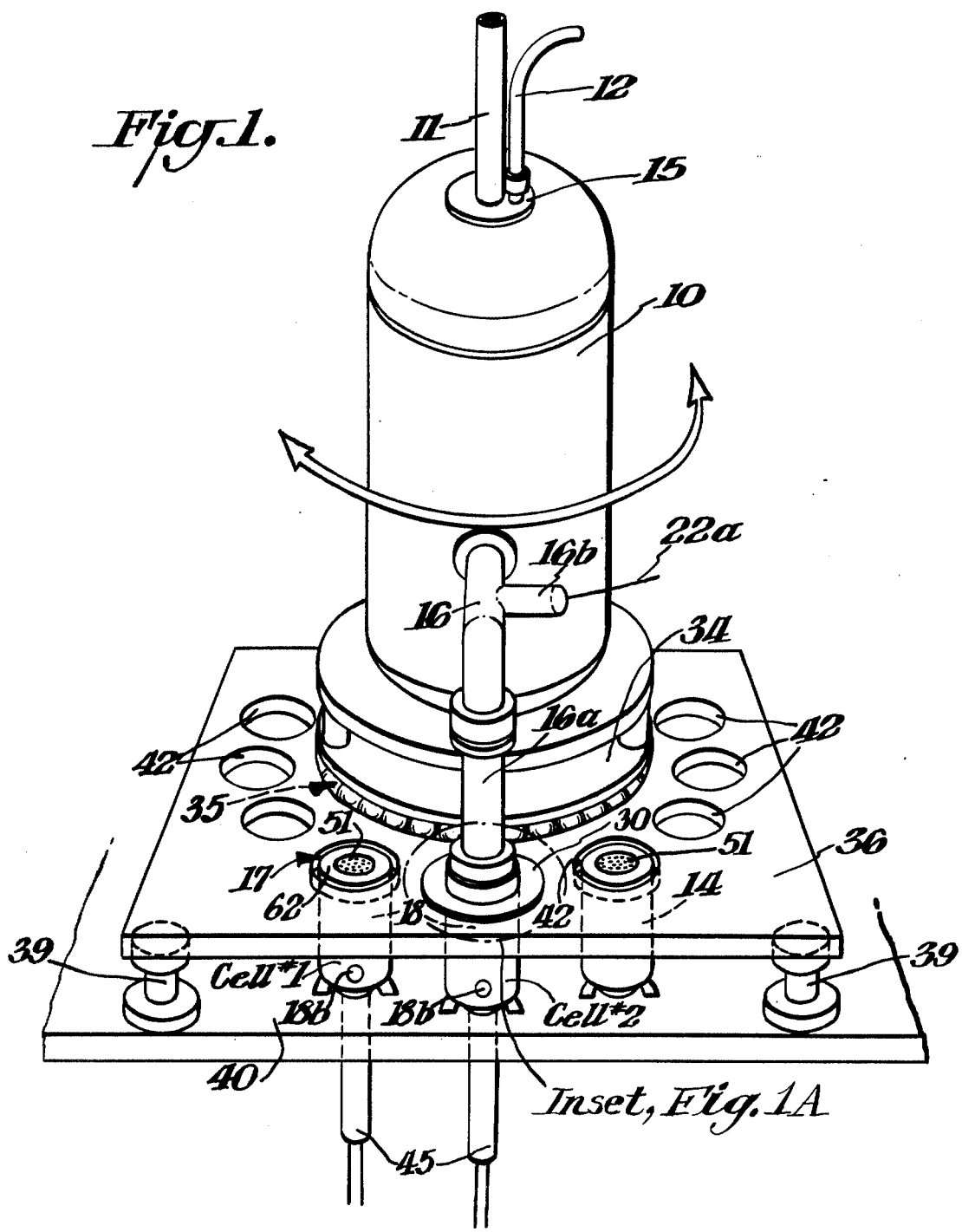

ON-STREAM CHEMICAL ELEMENT MONITOR

BACKGROUND OF THE INVENTION

The analytical technique of x-ray energy dispersive fluorescence analysis is well known and depends fundamentally on the ability to excite, by projecting primary radiation onto a sample, and thereafter accurately to measure the characteristic K and L x-rays emanating from the sample material. The radiation from each chemical element present in the sample has an essentially unique photon energy, and the intensity of each is a function of the quantity of that element.

In chemical manufacturing operations it is often advantageous to analyze successively a multiplicity of different sample streams drawn from different points in the process, and to do this rapidly on samples which are available as continuously flowing streams piped to the common analysis site. It is also frequently advantageous to analyze for chemical elements which are present in the sample streams as either solids or in the dissolved state. For example, catalytic metals are often utilized as solids slurries and the accurate analyses of these slurries by flow of the suspensions through analytical cells is often desired.

The advent of solid-state x-ray detectors of improved resolution and increased acceptance angle, in combination with electronic pulse analyzers of improved reliability, has expanded the applicability of x-ray fluorescence analysis to a great number and variety of manufacturing processes in the chemical industry.

One of the principal advantages of solid-state detector components for energy dispersive analysis is their multi-element detection capability for a wide range of energies and their conversion to characteristic voltage signals, allowing the intensities of many characteristic x-rays to be determined simultaneously. Also, more compact excitation radiation source-sample-detector geometries are permitted, while, at the same time, minimizing the required intensity of exciting radiation.

When samples exist as flowing liquids, they must be contained during the measurements in such a way as to satisfy, as well as take full advantage of, these improved geometric criteria. A problem of particular concern is the analysis of multiple flowing liquid samples in systems sharing the use of a single source-detector, since the cost and physical arrangement of individual source-detectors for this purpose is usually prohibitive. In each instance, the surface of the sample undergoing analysis must be maintained at a relatively fixed location with respect to both the radiation source and the detector past which the liquid is moving in a flowing motion, since it is well known that any recurrent variation of the sample surface with respect to the radiation source and detector can cause significant variations in intensity. Moreover, the materials of construction of the analysis cell, including the window portion, must be such that they will not interact with the flowing sample stream nor unduly absorb the incident and emitted radiation. These and other problems are solved by a combined sampling system and x-ray detection module in accordance with this invention.

BRIEF SUMMARY OF THE INVENTION

The invention is a practical source-sample-detector arrangement for radioisotope x-ray energy dispersive fluorescence analysis, and comprises a multiplicity of sample flow cells disposed in vertical and circular array, each having its window facing upwards with respect to a turreted, rotatable Dewar-preamplifier-downwardly directed detector-source module connected to a cryogenic liquid nitrogen ($LN_2$) supply through a rotatable seal into the Dewar.

The system has several outstanding features, among which are complete physical isolation of each vertical flowthrough cell from the associated source-detector mounting means, making the analysis essentially vibration-insensitive. Included integrally within the cell body is a metallic screen which serves the dual function of a reference material for maintaining pulse counting consistency, as well as a samplewindow support. The capability of rotationally indexing the source and detector from one sample stream to another greatly facilitates the overall process piping layout, as well as the accommodation of a non-flexible refill line for $LN_2$ supply to the Dewar. In general, the x-ray hardware, detector and excitation source are available commercially. The novel sampling system had, however, to be developed, since it must be adapted to the process piping.

DRAWINGS

Figure 2:
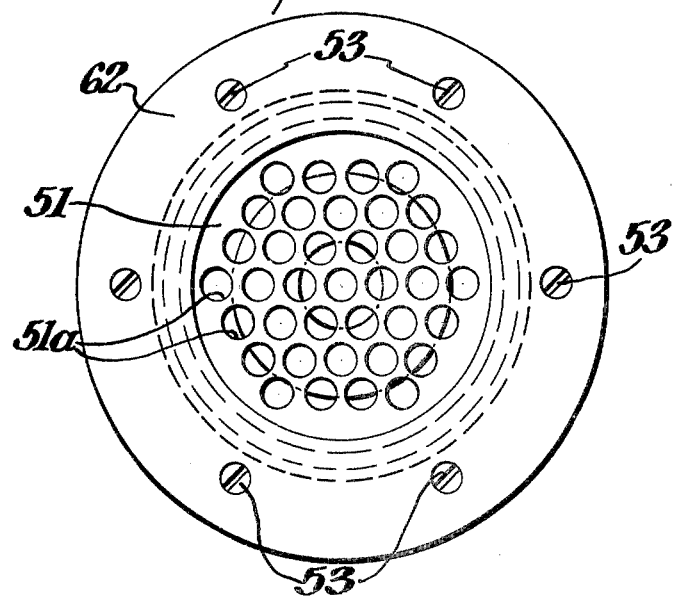
Figure 3:
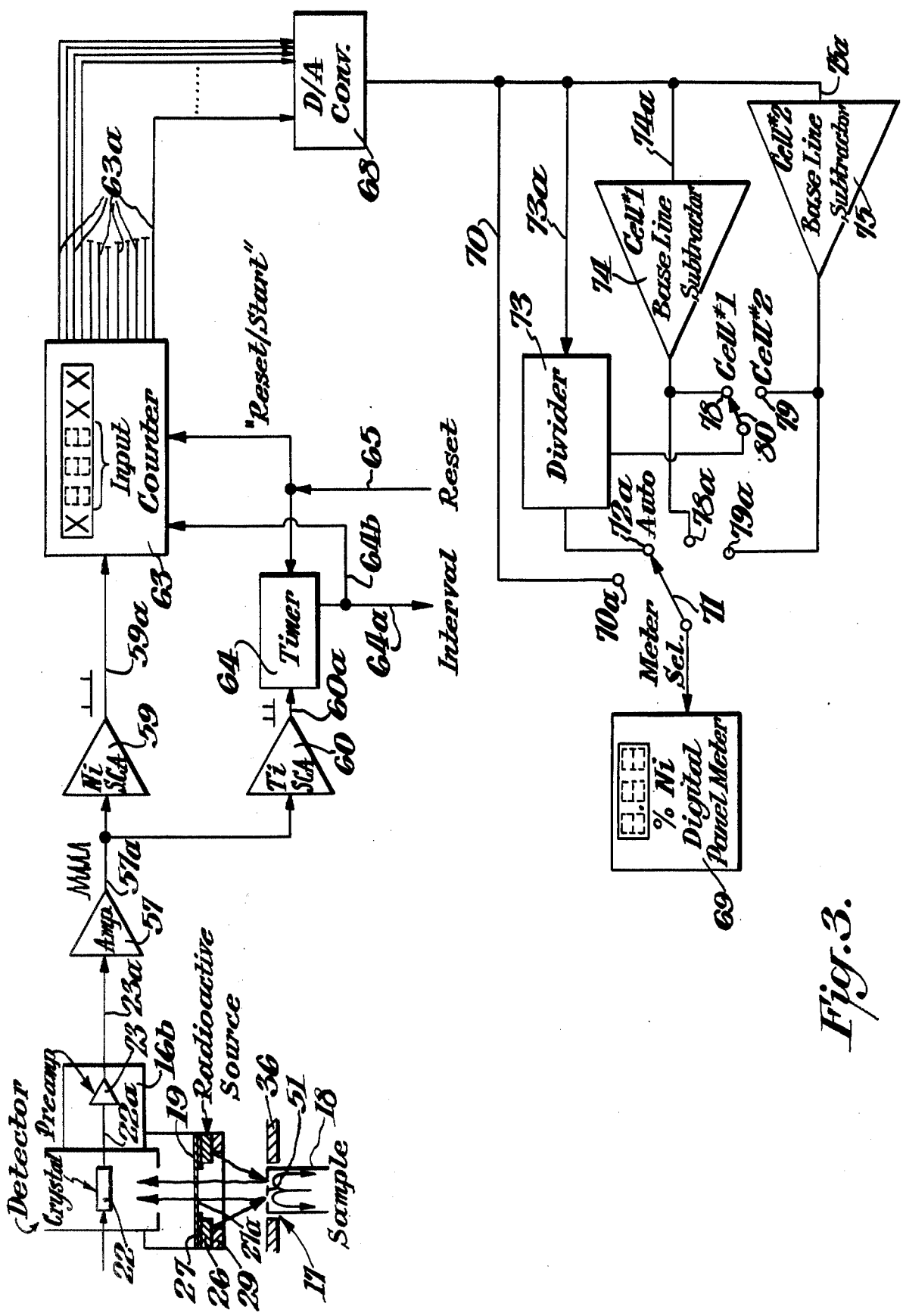

The following drawings constitute part of the specification, in which:

FIG. 1 is a partially schematic perspective view of the entire assembly of analyzer, sample cells, and support components for the apparatus of this invention, FIG. 1A is a vertical sectional view of the apparatus indicated in the inset of FIG. 1, FIG. 2 is a plan view taken on line 2—2, FIG. 1A, and FIG. 3 is a circuit diagram of a preferred circuit for effecting analytical readout with the apparatus of FIGS. 1–2.

Referring to FIGS. 1 and 1A, liquid nitrogen cooling of solid state detectors is necessary to reduce thermally created noise and also to prevent lithium migration in the silicon detector crystal 22. Therefore, a conventional Dewar flask 10 is provided, which is fitted with a liquid nitrogen fill tube 11 and a fill level detector tube 12, both of which open into the top of the Dewar flask through a conventional slip joint 15.

Dewar 10 is provided with an evacuated radial tubular housing 16 having a downwardly depending outboard extension 16a with its end directed toward the sample exposure heads 17 of the sample flow cells 18. A thin radiation permeable vacuum sealing beryllium window 19 closes off extension 16a.

As shown in FIG. 1A, a copper cold finger 20 extends from the interior of Dewar 10 nearly to the end of tubular extension 16a, and detector crystal 22, typically a planar crystal made from silicon doped with lithium, is attached to the depending end of cold finger 20, thereby maintaining the detector crystal at a low temperature approaching that of liquid nitrogen. It is also advantageous to maintain the pre-amplifier 23 of the signal processing circuit hereinafter described at low temperatures of the same order as the detector crystal 22. Therefore, there is provided a small tubular side extension 16b within which is housed pre-amplifier 23, as indicated schematically in FIG. 3. Electrical conductor 22a connects detector crystal 22 with pre-amplifier 23 and conductor 23a connects the latter with the remainder of the electrical circuit of FIG. 3.

Radiation source 26 is of generally annular shape, rounded on the underside peripherally of the central opening, typically cadmium 109 having a nominal strength of 10 millicuries. It is shielded from direct in-line exposure to detector crystal 22 by a shielding metal washer 27, the central opening 27a of which overlies sample exposure heads 17 during analysis. A metal cup-shaped bottom shield 29, drilled centrally at 29a for free passage of radiation to sample exposure heads 17, secured to 16a by set screw 31, completes the source-detector assembly. To this is attached an annular skirt piece 30, which is mounted at close clearance with respect to table 36 (typically, 0.020 inch) and protects the operator from scattered radiation leakage when the outboard extension 16a shifts from cell to cell.

The entire assembly of Dewar flask-source-detector and associated shielding hereinbefore described is supported on a rotatable table 34 which, in turn, is supported by a ball bearing assembly denoted generally at 35, the bearing assembly being mounted within a groove in stationary plate 36 with the upper portions of the balls rotating in a companion groove, not shown, machined in the underside surface of table 34.

Plate 36 is supported on conventional rubber shock mounts 39 disposed at all four corners which isolate the analysis equipment from the top of the table 40. Accordingly, it will be seen that the analyzer sub-assembly made up of Dewar 10 and its associated gear is mounted for free rotation about its vertical axis, so that outboard extension 16a and its source-detector can be easily swung circularly, as denoted by the double rotational arrow, to an analyzing position over any given sample flow cell 18. At the same time, shock mounts 39 isolate the analyzer from external vibrations or other shocks which exist in the manufacturing environment.

Plate 36 is provided with a convenient number of aperture through bore 42 disposed in circular array around the vertical axis of rotatable Dewar 10 at radii corresponding to the vertical axis of outboard extension 16a, so that the source-detector sub-assembly can be automatically indexed to coincidence with the vertical axes of each of the throughbores 42 at will.

Referring now to FIGS. 1A and 2 particularly, sample flow cells 18 can generally resemble the design shown in U.S. Pat. No. 3,354,308 and comprise an axially disposed upstanding sample supply tube 45 surmounted at its open upper end by an annular flow flattener element 46, over the top surface of which fluid samples are brought to even, radially outward flow. Flow cells 18 are independently supported from table 40 and disposed generally concentric with through bores 42 and out of peripheral contact therewith, to avoid any vibration or shock transmission from table 40 to plate 36. Sample fluid is continuously flowed to exhaust through the annular passage 18a communicating with discharge opening 18b, which optionally returns sample material to the manufacturing process or to waste, as desired, by tubing connections not detailed. Since the sample supply system is under pressure, it is necessary to seal off the sample cell exposure head 17 with a high strength radiation non-absorptive window 48, which can typically constitute a thin laminate of polytetrafluoroethylene, which, because of its resistance to chemical attack, is disposed on the inside, i.e., in contact with the sample fluid, and strong polyimide film backing on the outside. To safeguard against sample fluid leakage, it is preferred to machine the top surfaces of the walls of sample flow cells 18 with a circular ridge 47 against which abuts annular gasket 49.

Additional strength is conferred by perforate reference metal disc, or screen, 51 (typically about 0.1 cm thick) which is secured in position overlying window 48 by metal ring 52 held tightly to the top side of cell 18 by countersunk machine screws 53 engaging with tapped threads 53a.

Referring to FIG. 2 particularly, perforate reference metal discs (or screens) 51 are provided with precisely drilled openings 51a [typically, 0.312 inch (0.79 cm) dia.] arranged in regular hexagonal pattern, so that all cells are provided with equal reference metal areas [typically, 0.8 sq. in. (5 sq. cm) each] exposed to analytical radiation from source 26.

Typical component-to-component distances are:
source 26 to top of reference screen 51 = 1.5 cm ave.
detector 22 to top of reference screen 51 = 2.5 cm
detector 22 to plastic window 48 = 2.6 cm
source 26 to plastic window 48 = 1.6 cm ave.
detector 22 to beryllium window 19 = 0.75 cm.

Referring to FIG. 1, sample cell 14 is provided for grab sample analysis and, therefore, does not embody sample flow connections as shown for the sample cells 18. Sample cell 14 has its reference screen 51 attached as hereinbefore described for the sample cells 18 but is filled with sample through a supply opening in the lower end closed off with a screw cap, not shown.

Referring to FIG. 3, a preferred electrical circuit for the analysis monitoring of a typical element, in this example particulate nickel catalyst in slurry, referred to titanium metal utilized as screen 51 material, is described. As previously mentioned, pre-amplifier 23 generates output voltage pulses proportional to the collected charge from detector crystal 22 simultaneously for both analyzate and reference metal, but distinctive for each. This raw signal is input to variable gain amplifier 57, which functions to increase the pre-amplifier output signal-to-voltage levels compatible with analog-to-digital conversion and provides band-pass characteristics which enable signal extraction with the least amount of noise. The voltage output of amplifier 57 sent via output conductor 57a is an undifferentiated composite of Ni and Ti signals which is shown, schematically, as a relatively high frequency pulse train adjacent to conductor 57a.

This output is sent simultaneously to two parallelconnected single-channel analyzers, which embody amplifiers 59 and 60, each of which imposes a preselected upper and lower energy limit on the input pulses, thereby allowing all pulses between these limits to be counted. For the circuit detailed, amplifier 59 is shown as the Ni pulse segregator, which pulses are denoted as having a characteristic amplitude represented by the spike signal drawn adjacent to output line 59a. Similarly, amplifier 60 is the Ti pulse segregator, which outputs pulses of similar amplitude to the Ni channel, but of different frequency, as denoted by the spike signal drawn adjacent output line 60a.

The Ni pulses are routed to pulse counter 63, whereas the Ti pulses go to timer 64, which is in reality also a counter, the purpose of which is to establish a preset x-ray measurement interval in terms of Ti pulse total which maintains consistency over a given succession of Ni analyses.

Establishment of a consistent analysis time is necessary for three principal reasons: (1) pulse generation and detection by the source-detector module is continuous in time and therefore must be effectively interrupted in order to read out meaningful concentration data, (2) the source half-life of cadmium 109 is of the order of approximately 453 days, so that the rate of count accumulation is continuously slowly decreasing, necessitating progressively longer count-up intervals for any preselected total number of counts received from a given radiation source 26, and (3) motion of the source-detector toward or away from the sample reference due to the resilient shock-mounting feature can cause changes in the measurement time.

These problems are solved by utilizing pulse counting timer 64 to establish the operational counting time span for both counter 63 and timer 64. This is accomplished by setting the count limit of timer 64 to a level in terms of accumulated Ti reference metal counts during which it is known experimentally that a sufficiently large number of analyzate metal (Ni) counts will be simultaneously acquired to accurately determine the Ni content analyzed for.

At this instant a signal is output through line 64a that certifies that a single analysis cycle is completed and that a time interval is provided during which Dewar flask 10 and its appurtenances can be indexed to the next-following analysis position. This signal is simultaneously routed to counter 63 via line 64b, thereby halting its count-up, so that the analysis total reached at this instant represents the Ni analysis just completed. When Dewar 10 and its appurtenances has completed indexing to the next sample flow cell 18 in order, an electrical signal is directed through reset line 65 from a source not shown which simultaneously resets counter 63 and timer 64, commencing a new analysis cycle.

The efficacy of a simultaneously acquired reference metal pulse count as an analysis interval-establishing agency is shown by the following mathematical analysis:

Let $I_i$ be the detected x-ray flux for a given element in analysis (e.g., particulate Ni as a slurry in a hydrocarbon liquid) in counts/time, whereupon $$I_i = g_i E_i C_i \phi_s(t)$$

where $g_i$ is a geometry factor from sample to detector, $E_i$ is the excitation efficiency of element i in the sample, $C_i$ is a function of the concentration of chemical element i in the sample, and $\phi_s(t)$ is the flux of exciting radiation per unit area excited.

Then, for the case where Ni is analyzed for and Ti is the reference metal:

$$\frac{I_{Ni}}{I_{Ti}} = \frac{g_{Ni} E_{Ni} \phi_s(t) C_{Ni}}{g_{Ti} E_{Ti} \phi_s(t) C_{Ti}}$$

$$= \alpha C_{Ni} \text{ where}$$

$$\alpha = \frac{g_{Ni} E_{Ni}}{g_{Ti} E_{Ti} C_{Ti}}, \text{ from which}$$

$$I_{Ni} = I_{Ti} \alpha C_{Ni}$$

Thus, by always counting a fixed number of Ti x-rays, $I_{Ni}$ is proportional to $C_{Ni}$, since $\alpha$ is a constant.

Moreover, $\alpha$ remains substantially constant as the sample-plane-to-detector distance changes, which compensates for transitional and/or vibrational displacements of individual apparatus components in the course of analytical service, because:

$g_{Ni} \alpha 1/r^2_{Ni}$ where $r_{Ni}$ is the distance from the detector to surface of sample.

$g_{Ti} \alpha 1/r^2_{Ti}$ where $r_{Ti}$ is the distance from the detector to the reference surface.

In a typical instance where the reference metal screen is 0.01 inch closer to the detector 22 than the sample surface, $r_{Ti} = r_{Ni} - 0.01$ inch so that where $r_{Ni} \simeq 1$ inch, Then $$\frac{g_{Ni}}{g_{Ti}} = \frac{r^2_{Ti}}{r^2_{Ni}} = \frac{(r_{Ni} - 0.01)^2}{r^2_{Ni}}$$

$$= \frac{r^2_{Ni} - 2(0.01)r_{Ni} + 0.0001}{r^2_{Ni}}$$

$$= 1 - \frac{0.02}{r_{Ni}} - \frac{0.0001}{r^2_{Ni}}$$

So, near $r_{Ni} \simeq 1$ inch, $g_{Ni}/g_{Ti} = 0.9799$ whereupon, as $r_{Ni}$ changes by 0.25 inches, or 25%, the ratio changes to 0.9735, and $g_{Ni}/g_{Ti}$ changes by only 0.65%, to the second order.

Counter 63 is provided, typically, with twelve output lines 63a, only four of which are detailed fully in FIG. 3, these being collected in a cable which inputs the Ni analytical signal to digital-to-analog converter 68. The analog voltage output from D/A converter 68 is then routed via a switching circuit which, in turn, supplies per cent Ni digital indication meter 69.

The switching circuit incorporates a direct connection, via line 70, to the first of four contacts, 70a, which are provided for circuit closure by meter selector switch 71. Direct connection through line 70 is useful in preliminary tuning of the apparatus during installation; however, normal analytical service is effected through the "Auto" contact 72a.

Individual sample flow cells 18 can display detectible initial base line readings when they are subjected to analysis with zero analyzate element in the liquid sample stream but with the perforate reference metal discs 51 in place.

Following the carrying out of the D/A conversion of analyzate element counts to a voltage analog signal representative of the counts of analyzate element present in the liquid sample, the voltage output from block 68, typically 0 to −10 volt analog voltage, is conducted to analog computational circuitry wherein one of two possible computations is carried out, depending on whether a linear conversion from analyzate counts to percentage analyzate can be assumed.

If such a conversion cannot be made (e.g., if the calibration curve is hyperbolic), the computation is done in divider block 73, which is a linear integrated circuit analog divider chip of conventional design comprising suitable operational amplifier circuitry with voltage offset and feedback provision for performing the operation $$\frac{V_{Ni}}{\alpha(V_{Ni} - V_{BG})} = \% \text{ Ni voltage,}$$

where $V_{Ni}$ is the analog voltage representative of the counts of analyzate element, $V_{BG}$ is the voltage with zero analyzate element in the liquid sample, and $\alpha$ is a calibration constant.

If a linear conversion can be assumed, then the computation performed is given by $$\alpha(V_{Ni} - V_{BG}) = \% \text{ Ni voltage,}$$

which can be carried out by conventional analog subtractor modules 74 and 75, one for each sample cell, since the scale conversion will differ somewhat from cell to cell. The electronic operation entails a simple subtraction of the background voltage $V_{BG}$ and a scaling of the overall difference.

In making the analysis for nickel, the latter computation has been found satisfactory. Thus, divider circuit 73 can be shorted out by joining junctions 72a and 80, providing a direct feed from the subtractors to the % Ni meter.

Finally, contacts 78a and 79a, selectively closed by meter selector switch 71, are provided for numerical indication by meter 69 of individual cell base line reading magnitudes should this be desired.

We claim:

1. A method of energy dispersive fluorescence radiation analysis using a radiation source, a reference metal, a sample and a fluorescence radiation detector comprising subjecting an elemental sample to be analyzed and a reference metal to simultaneous exposure to x-ray irradiation from a radioactive source such that the surfaces of said reference metal and said sample are in rigid juxtaposition to each other and further such that the detector is in non-rigid juxtaposition to said surfaces, detecting the total number of fluorescence radiation pulses from said exposure, segregating the pulses due to said elemental sample to be analyzed from those pulses due to said reference metal and basing the time duration of the analysis cycle upon a preselected accumulated number of said pulses due to said reference metal.

2. In an on-stream energy dispersive x-ray fluorescence radiation analyzer for sequential analysis of a preselected elemental ingredient in liquid media, a radiation source-sample-detector arrangement comprising
    a generally horizontal plate supported by shock mounts,
    a rotating table carried by said plate, said rotating table supporting a vertically disposed Dewar cryogenic flask having a slip-joint connection at the top end for supply of liquefied coolant medium to said flask,
    a radial tubular housing shielding the cold finger of said Dewar cryogenic flask having a downwardly depending outboard extension terminating in a fluorescence radiation-permeable window,
    a fluorescence radiation detector mounted in contact with said cold finger within said downwardly depending outboard extension transverse thereof and near the terminal end, with radiation sensing surface directed downwardly toward said fluorescence radiation-permeable window,
    an annular housing attached to the outboard end of said extension adjacent the top of said plate fitted with a radioactive source disposed concentric with the bore of said extension and shielded from direct exposure to said detector so that radiation emitted by said source impinges at a level corresponding generally to the top plane of the liquid medium incorporating elemental analyzate hereinafter mentioned,
    a multiplicity of through-bores drilled through said plate in circular array with respect to the vertical axis of said Dewar flask, and
    individual axially-reverse flow cells for x-ray radiation exposure of said liquid media incorporating elemental analyzate disposed vertically within each said through-bore but out of contact with the peripheries thereof, the tops of said flow cells being generally disposed within said through-bores and closed with a source radiation-permeable seal cap surmounted by a metal screen fluorescing radiation distinguishable from the radiation fluoresced by said elemental analyzate in said liquid media, fluoresced radiation from said elemental analyzate content of said liquid media and said metal screen being directed upward through said extension to said radiation detector.

3. An on-stream energy dispersive x-ray fluorescence radiation analyzer for sequential analysis of the metal content in liquid media according to claim 2 provided with an electrical circuit responsive to said fluorescence radiation detector provided with means processing the total number of fluorescence radiation pulses generated by said radiation detector, means segregating the pulses due to said elemental sample to be analyzed from those pulses due to said metal screen as reference metal and means basing the time duration of analysis cycles upon a preselected accumulated count of said pulses due to said reference metal.

4. An on-stream energy dispersive x-ray fluorescence radiation analyzer for sequential analysis of the elemental content in liquid media according to claim 2 provided with an electrical circuit responsive to said fluorescence radiation detector embodying two parallel-connected single channel pulse analyzers, a preselected one of which segregates the pulses due to said elemental analyzate whereas the other one of said pulse analyzers segregates the pulses due to said metal screen as reference metal, a pulse counter counting said pulses due to said elemental analyzate, a timer accumulating a count of said pulses due to said metal screen as reference metal, said timer being connected to said pulse counter in time control circuit therewith, and means down circuit from said pulse counter indicating the concentration of said elemental ingredient in said liquid media.

5. An on-stream energy dispersive x-ray fluorescence radiation analyzer for sequential analysis of the metal content in liquid media according to claim 2 wherein said metal is nickel.

* * * * *